United States Patent
Ygartua et al.

(10) Patent No.: US 7,801,713 B1
(45) Date of Patent: Sep. 21, 2010

(54) GENERATING A MODEL USING GLOBAL NODE OPTIMIZATION

(75) Inventors: Carlos L. Ygartua, Palo Alto, CA (US); Leonid Poslavsky, Belmont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 913 days.

(21) Appl. No.: 11/561,245

(22) Filed: Nov. 17, 2006

(51) Int. Cl.
*G06G 7/48* (2006.01)
*G06F 17/50* (2006.01)
(52) U.S. Cl. .............................................. 703/6; 716/2
(58) Field of Classification Search .................. 703/6; 716/2; 438/7, 32
See application file for complete search history.

(56) References Cited

U.S. PATENT DOCUMENTS

| | | | |
|---|---|---|---|
| 6,649,075 B1 | 11/2003 | Buie et al. | |
| 6,734,967 B1 | 5/2004 | Piwonka-Corle et al. | |
| 7,049,844 B1 | 5/2006 | Ygartuua | |
| 2004/0008349 A1 | 1/2004 | Norton | |
| 2005/0057755 A1* | 3/2005 | Johnson et al. | 356/446 |
| 2006/0050283 A1* | 3/2006 | Hill | 356/512 |
| 2006/0126079 A1* | 6/2006 | Bareket et al. | 356/625 |

\* cited by examiner

*Primary Examiner* — Paul L Rodriguez
*Assistant Examiner* — Andre Pierre Louis
(74) *Attorney, Agent, or Firm* — Bever, Hoffman & Harms, LLP; Jeanette S. Harms

(57) ABSTRACT

A global node optimization (GNO) technique can generate a model for a planar multiple layer film stack structure, e.g. a binary grating structure. In this technique, after obtaining spectra and target thicknesses from one or more wafers, a continuous film approximation (CFA) and a grating factor (GF) set are identified. A model using the CFA and the GF set is optimized by simultaneously fitting a plurality of the spectra while minimizing error compared to the target thicknesses. After simultaneously fitting all of the spectra, a GNO stack is created. A GNO recipe is then created using the GNO stack. Notably, a tool implementing the GNO technique uses minimal modeling capabilities and computational resources.

10 Claims, 5 Drawing Sheets

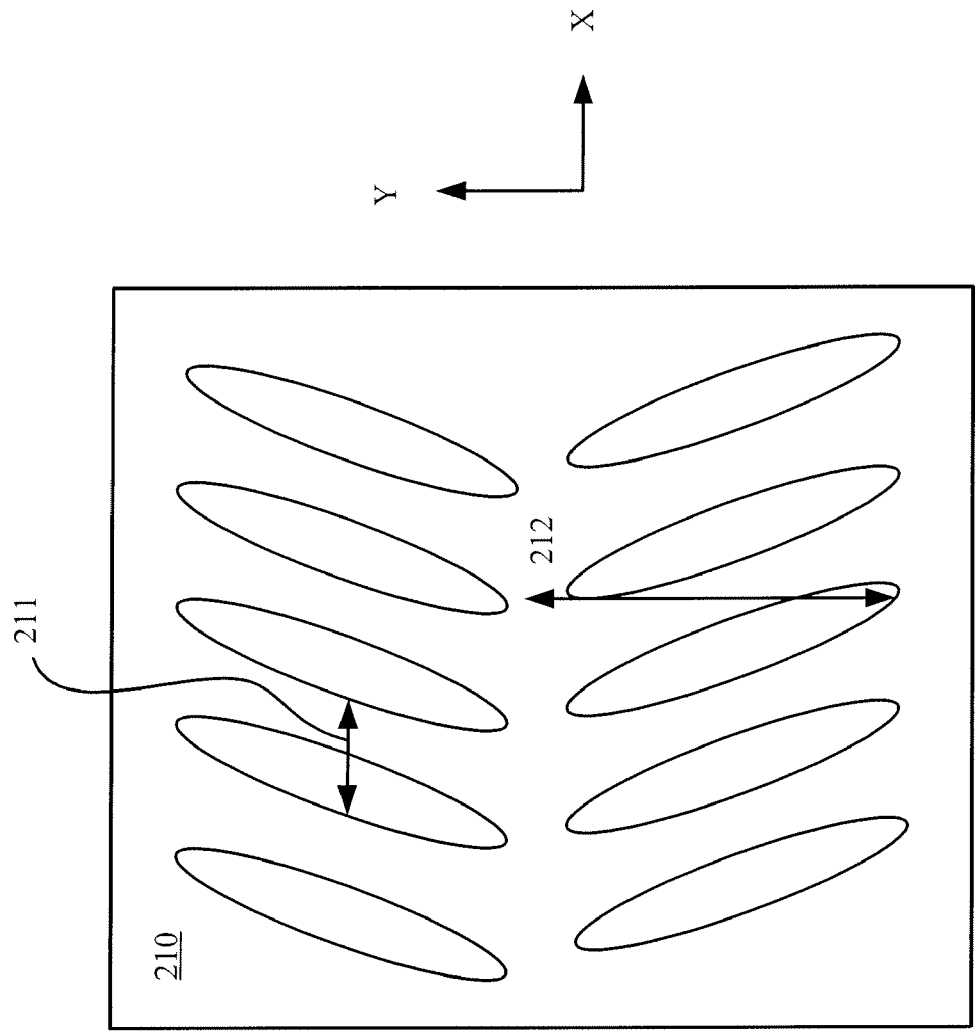

GENERATING A MODEL USING GLOBAL NODE OPTIMIZATION

BACKGROUND OF THE INVENTION

1. Field of the Invention

The present invention relates to a technique for generating a model for a planar multiple layer film stack structure and in particular to modifying this model for a binary grating.

2. Related Art

Examples of multiple layer binary grating structures are found on integrated circuit devices during various stages of their production. For example, arrays of periodic structures used to form various parts of those devices typically form one or more binary multiple layer grating structures. FIG. 1 illustrates a cross-section of an exemplary binary multiple layer grating structure (hereinafter grating structure) 100 formed on a silicon (Si) substrate 101. In this case, each film stack of grating structure 100 includes a vertically-inclined, Si member 102, a thermal silicon dioxide (SiO2) film 104, and a silicon nitride (SiN) cap 103. An SiO2 (oxide) layer 105 is formed over and completely covers the film stacks.

Note that grating structure 100 is shown in idealized form with film stacks having straight edges and constant (or constantly varying) thickness. In a real chip, each film stack typically has irregular edges and large local thickness variations (e.g. on the order of 100 Å per mm). Thus, determining an accurate thickness range for binary layers of grating structure 100 remains a difficult problem in the chip fabrication industry.

An accurate thickness determination can be critical in performing certain processes. For example, accurately determining the thickness of a binary layer including SiN caps 103 can become critical when oxide layer 105 is polished, e.g. using chemical-mechanical polishing (CMP). That is, one step in a typical fabrication recipe is to polish oxide layer 105 to a predetermined thickness, which is measured from the top of SiN caps 103. To the extent that the binary layers of grating structure 100 vary in thickness, determining when to stop polishing oxide layer 105 becomes uncertain.

Note that spectroscopic ellipsometry (SE) can measure the changes in the state of polarization of light upon reflection from a surface to determine the thicknesses of multiple continuous films (i.e. thin homogeneous layers), wherein each continuous film is larger than the light spot used to analyze that continuous film. Unfortunately, grating structure 100 comprises multiple "discontinuous" (i.e. non-homogeneous) films, thereby rendering the relatively simple SE models inaccurate for measuring the thickness of grating structure layers.

In another known technique, full diffraction theory can be used to model a grating structure. However, the computational requirements for full diffraction modeling may be too large for some commercial applications.

Therefore, a need arises for a technique to accurately measure and estimate the thickness of various layers of a grating structure while minimizing computational resources.

SUMMARY OF THE INVENTION

A global node optimization (GNO) technique that can generate a model for a planar multiple layer film stack structure, e.g. a binary grating, is provided. This GNO technique can start by designating a design of experiment (DOE), e.g. one or more wafers. Both spectra and target thicknesses can be obtained from the DOE. At this point, a continuous film approximation (CFA) and a grating factor (GF) set can be identified.

In accordance with one aspect of the present invention, a model using the CFA and the GF set can be optimized by simultaneously fitting a plurality of the spectra while minimizing error compared to the target thicknesses. If the optimizing is not acceptable (i.e. the difference between theoretically predicted and measured spectra exceeds a predetermined threshold), the GNO technique can return to obtaining spectra if the spectra is suspect, obtaining target thicknesses if the target thicknesses are suspect, or identifying the CFA and the GF set if a different mixing model or a different GF set can be used to obtain more accurate results.

In one embodiment, the spectra can be obtained from at least 10 die on a wafer. In another embodiment, the spectra can include ellipsometric spectra in a wavelength range of 240-800 nm. In yet another embodiment, the spectra and target thicknesses can include in-die measurements.

After simultaneously fitting all of the spectra, a GNO stack can be created. The GNO stack can include mathematical models that describe physical properties of the film stack structure. A GNO recipe can then be created using the GNO stack. The GNO recipe can include ordered instructions using the mathematical models of the GNO stack to achieve at least one computational result. Notably, a tool implementing the GNO technique uses minimal modeling capabilities and computational resources.

BRIEF DESCRIPTION OF THE FIGURES

FIG. 2C illustrates an exemplary off-normal orientation of a layout for a grating structure.

DETAILED DESCRIPTION OF THE FIGURES

In accordance with one aspect of the invention, a grating structure can be approximated by treating the binary layers of the grating structure as continuous films (hereinafter referenced as continuous film approximations (CFAs)). Diffraction effects can be accounted for by introducing corrections at the interfaces of each binary layer. These corrections, called grating factors (GFs) herein, are applied to the Fresnel reflection and transmission coefficients associated with the film interfaces for the binary layer. In general, the diffraction effects are a function of the film properties (e.g. thickness and refractive index (RI)) in addition to the binary layer dimensions.

Figure 1:
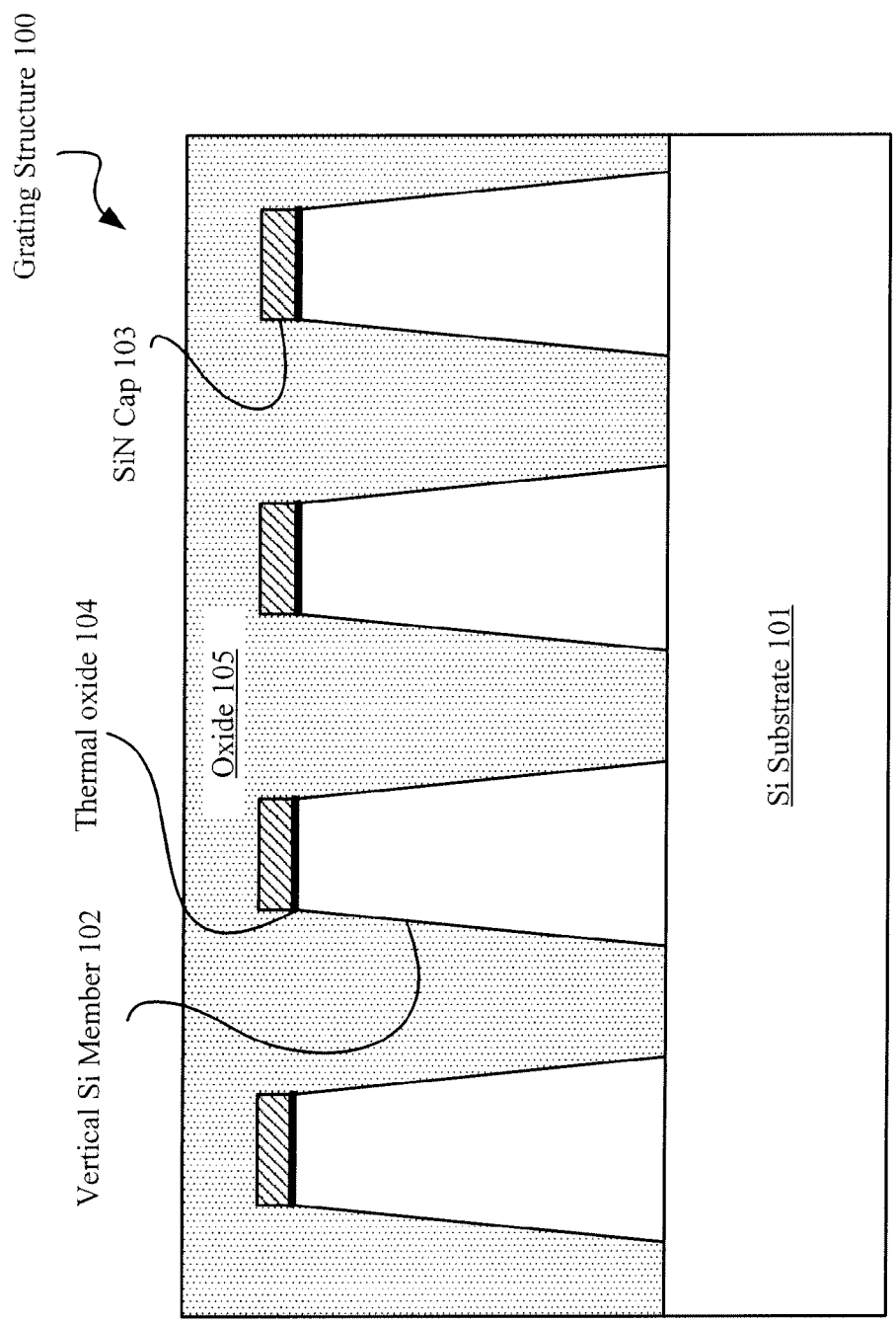
FIG. 1 illustrates a cross-section of a simplified binary multiple layer grating structure.
Figures 2A, 2B:
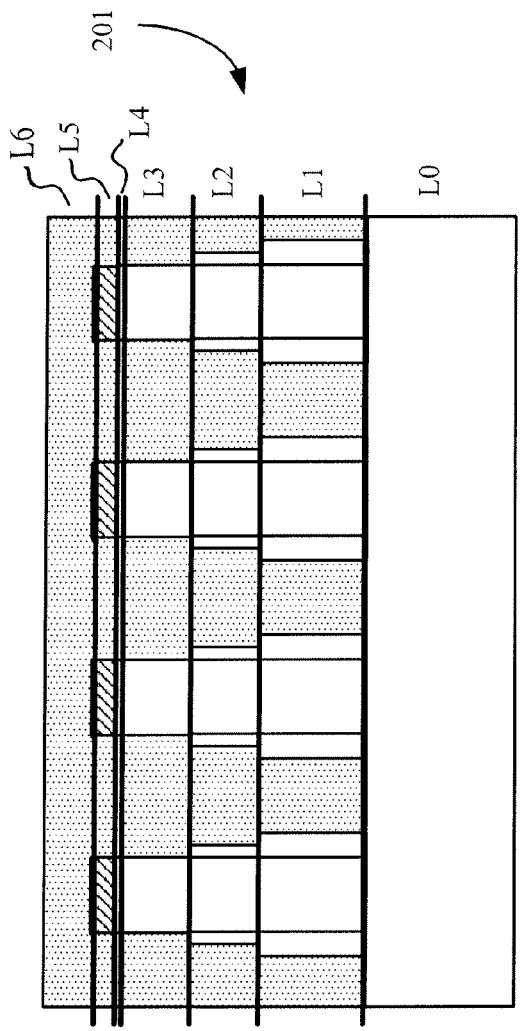
FIG. 2A illustrates a film stack model of the grating structure of FIG. 1. In this case, the film stack model includes seven binary layers L0-L6.
FIG. 2B illustrates a model summary table corresponding to the film stack model of FIG. 2A.

FIG. 2A illustrates a film stack model 201 of binary multiple layer grating structure 100 (FIG. 1) that is divided into seven binary layers: L0-L6. A binary layer is defined by the refractive index (RI) dispersion versus wavelength of the material in each region and the relative dimensions of the regions (or fractional amount of each material). FIG. 2B illustrates a model summary table 202 corresponding to film stack model 201. In this embodiment, model summary table 202 indicates each binary layer (L0=0, L1=1, etc.), whether a grating factor has been applied to each binary layer, the layer's (i.e. film's) name (in this embodiment comprising constituent materials), and the thickness of each binary layer.

Model summary table 202 also indicates average variations in trench dimensions versus depth, i.e. using a fraction f that indicates the amount of oxide in the binary layer (for example, a fraction 0.50 would indicate that half of the material in that binary layer is oxide, whereas a fraction of 0.25 would indicate that one-quarter of the material in that binary layer is oxide). In this grating structure, the fraction of oxide in the binary layers decreases as the trench narrows toward the substrate (i.e. binary layer L0). Therefore, as can be seen in film stack model 201, the film stacks are isotropic in the plane of incidence.

Of importance, a spectroscopic ellipsometry (SE) measurement is advantageously sensitive to the thickness and refractive index (RI) throughout a grating structure. For example, referring back to grating structure 100 of FIG. 1, the oxide of oxide layer 105 is completely transparent (i.e. k=0), the silicon nitride of SiN caps 103 is transparent over most of the spectrum, and the silicon of vertical Si members 102 is partially transparent ($\lambda$>450 nm). Therefore, each binary layer of grating structure 100, which is shown in film stack model 201 can be characterized as having two distinct regions, called line and space-fill (the line region including partially transparent materials and the space-fill region including only transparent materials). The line and space-fill regions can be treated as a single continuous layer with an RI that is the fractional sum of the RI of the constituent materials, wherein the fractions are the volume fraction of the line and space-fill regions (see e.g., fraction f of model summary table 202 in FIG. 2B).

The CFAs can advantageously leverage the fact that the period, i.e. the pitch, of the grating structure can correspond to UV wavelengths and that the silicon can be absorbing in the W. Wavelengths greater than the pitch do not have sharp spectral diffraction effects. Therefore, longer wavelengths "see" the grating structure more like a continuous film.

Note that the pitch of a grating structure may differ significantly based on orientation. For example, FIG. 2C illustrates an exemplary off-normal orientation of a layout 210 for a grating structure. In this embodiment, the pitch 211 in the X direction (e.g. on the order of 50 nm) is significantly less than the pitch 212 in the Y direction (e.g. on the order of 350 nm). Notably, although the average grating layer effective refractive index (RI) is independent of orientation, the spectra and diffraction effects can vary with orientation. For example, the zero order diffraction peak wavelength position varies with the pitch (i.e. periodicity) in the direction of the plane of incidence. In one embodiment, the orientation with the minimum pitch is used for both spectra measurement and GF determination.

In accordance with one aspect of the invention, a global node optimization (GNO) technique can be used to simultaneously fit multiple spectra from samples that represent the process range and possible excursions. This GNO technique can advantageously yield accurate results while minimizing computation resources.

Figure 3:
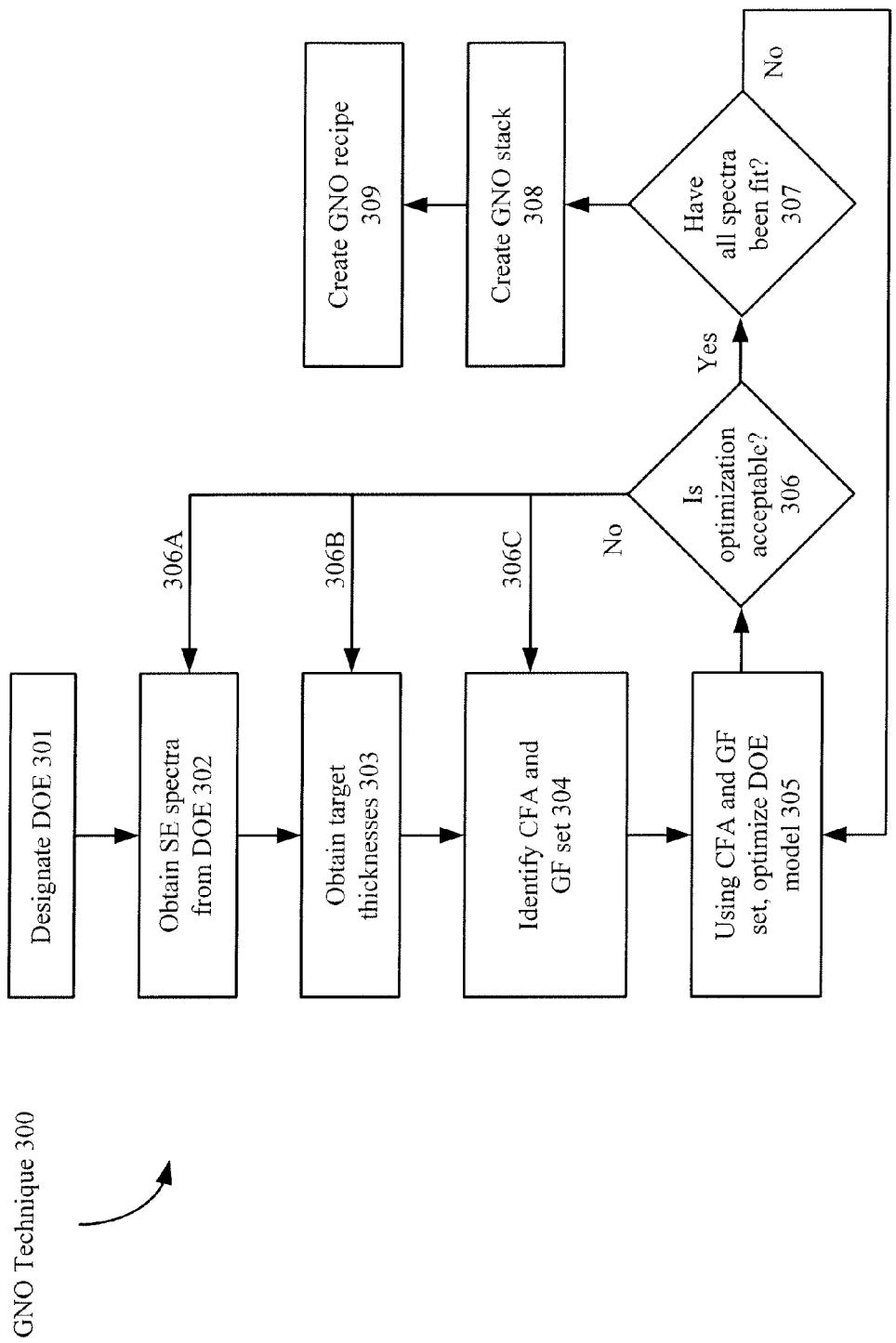
FIG. 3 illustrates an exemplary global node optimization (GNO) technique for creating a GNO recipe.

FIG. 3 illustrates an exemplary GNO technique 300 for creating a GNO recipe. In technique 300, a design of experiment (DOE) can be designated as an input in step 301. Note that the DOE could include one or more wafers of a lot. For example, if one wafer is representative of the wafer lot, then samples from just that wafer could be used in one embodiment. However, because many processes may have excursions, other embodiments could designate multiple wafers to ensure a quality DOE.

In step 302, SE spectra can be obtained from samples of that DOE. In one embodiment, the samples could include 10-15 die out of each wafer (which has 100-200 die). Note that fewer or more samples could be used based on the expected variation across the wafer.

Typically, ellipsometric spectra or reflectance spectra can be used. In one embodiment, ellipsometric spectra in the wavelength range of 240-800 nm can be measured at the same angle of incidence for the light. In another embodiment, multiple types of spectra, wavelength ranges, and/or angles of incidence can be used.

In order for the SE measurement to represent the average thickness over the size of the spot, the grating structures of the samples should be small relative to the spot size used in the SE. For example, if the spot size is 900-250 $\mu m^2$ and the pitch is 0.4 $\mu m$ (assuming that the x and y pitch is the same), then the SE measurement would represent the average thickness of a binary layer including 10,000 grating structure cells. In one embodiment, at least ten grating structures should be within the SE spot for accurate GNO results to be obtained.

In step 303, target thicknesses of the various materials in the film stacks (e.g. silicon, SiO2, and SiN) of these samples can also be obtained. For example, SEM measurements can be taken of the designated samples, wherein the measurements could have a predetermined tolerance (e.g. +/−15% tolerance). In one preferred embodiment, the samples designated for steps 302 and 303 include in-die samples.

Note that test structures in the scribe lines could be used for samples in steps 302 and 303. However, these test structures can be simplified and/or designed to accommodate measurement technology. For example, test structures can be built as long structures that are approximated as infinite (i.e. much larger than the spot size). Moreover, the scribe lines typically have no underlying structures, e.g. vias, etc., under the test structures (or the scribe lines have at least carefully controlled underlying layers). Therefore, using in-die samples advantageously yield SE spectra and target thicknesses that are significantly more accurate, i.e. more representational of the DOE, than if samples of test structure in the scribe lines are used.

In step 304, a continuous film approximation (CFA), i.e. a mixing model, can be identified. Exemplary mixing models include, but are not limited to, Bruggeman Effective Media Approximation (BEMA) and line/space fill. BEMA treats a plurality of materials as an alloy, i.e. as different materials mixed together perfectly, and is a non-linear model. In contrast, line/space fill is a linear model that assumes separate regions of different materials.

Step 304 can further identify a grating factor (GF) set, wherein a GF can be any functional representation of any function (wherein each function typically includes a small number of parameters to vary the function). The derivation of a GF is described in further detail in U.S. patent application Ser. No. 10/859,637, entitled "Optical Metrology On Patterned Samples", filed on Jun. 2, 2004 for KLA-Tencor Corporation, which is incorporated by reference herein.

Preferably, the CFA minimizes the role of the GFs. Therefore, in an initial iteration of step 304, the GFs are assumed to be zero. Non-zero GFs (0<GF$\leq$1) can be used in subsequent iterations of step 304, if necessary. Ideally, each GF should be as close to zero as possible. An optimized GF set from the binary layers allows all the spectra to be fitted over a range defined by known values of film stack parameters, such as the thickness of each layer as provided by step 303. The known film stack parameters are nodes (or calibration points) in relation to the set of variables to be optimized, which are other film stack parameters (e.g. RI or the fraction of space-fill) and the variables associated with the GFs. In one embodiment, a GF lookup model can be used to determine the appropriate GF set, wherein the GF lookup model can advantageously take into account diffraction variables that vary with thickness, grating dimensions, or scattering.

In step 305, using the identified CFA and GF set, a DOE model can be optimized. This optimization refers to modifying the model for the grating structure to fit the actual spectra (i.e. SE spectra from step 302) with minimal error compared to the actual data (i.e. the target thicknesses from step 303). As optimization occurs, i.e. a plurality of the spectra are simultaneously fitted, the fractions of materials present in the binary layers can float as variables until optimized values of the fractions can be determined.

Usually in an initial iteration of step 305, only a subset of the spectra is fit. For example, if 9 samples of the DOE are used, then step 305 may fit spectra from 3 out of the 9 samples. Note that the average distribution of the 3 samples should capture the DOE distribution, i.e. the subset should be a sampling that follows the statistics of the DOE. For example, in one embodiment, the subset of samples could include the thinnest thickness of the layers, the thickest thickness of the layers, and an average thickness of the layers.

If the optimization is unacceptable (i.e. the difference between theoretically predicted and measured spectra exceeds a predetermined threshold), as determined in step 306, then technique 300 can selectively loop back to various previous steps. For example, in one embodiment, where the SE spectra is suspect, technique 300 can loop back to step 302 (loop 306A). In another embodiment, where the target thicknesses are suspect, technique 300 can loop back to step 303 (loop 306B). In yet another embodiment, technique 300 can loop back to step 304 (loop 306C) to identify a different mixing model and/or set of different GFs.

Figure 4:
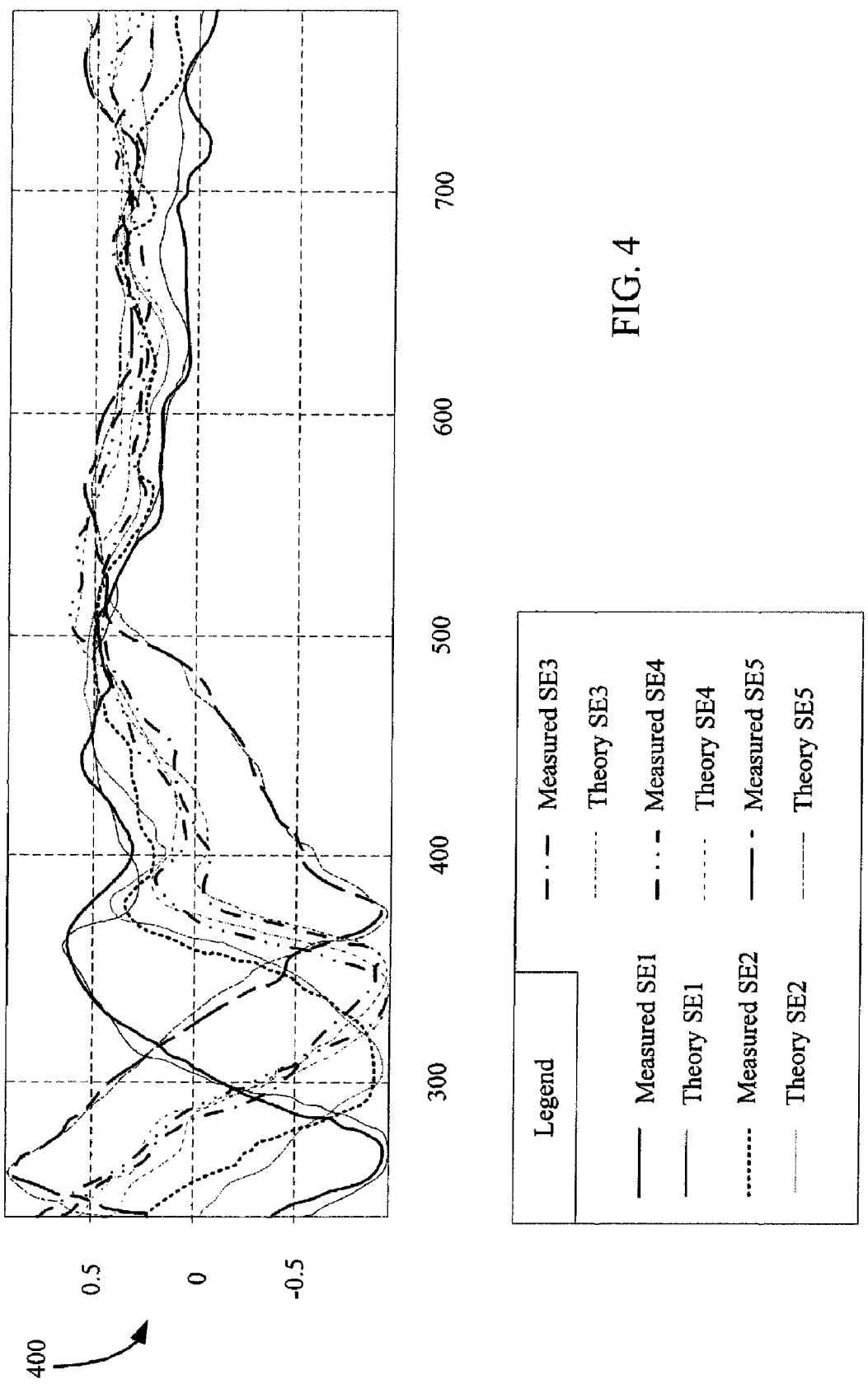
FIG. 4 illustrates a graph of an exemplary ellipsometric spectra fit for a global node optimization. In this graph, five spectra SE1-SE5 are fitted.

If the optimization is acceptable, as determined in step 306, then step 307 determines whether all spectra have been fit. If not, then technique 300 can return to step 305 to optimize the DOE using additional samples. FIG. 4 illustrates a graph 400 of an exemplary ellipsometric spectra fit for a global node optimization. In graph 400, five spectra (SE1-SE5) have been fitted. The legend for graph 400 designates the lines patterns for both the measured and theoretical spectra.

If all spectra have been fit, then step 308 creates a GNO stack. This GNO stack includes the mathematical models (i.e. a mathematical construct of a set of equations) that describe the physical properties of the film stack. Notably, these mathematical models can be used to estimate the parameter values of unknown samples that fall within the range defined by the nodes, i.e. the DOE samples. The accuracy of the estimate depends on the accuracy and relative spacing of the nodes.

Step 309 creates a GNO recipe. This GNO recipe can include a set of instructions (and their sequence to be performed) for using the mathematical models of the GNO stack to achieve a final result (e.g. a set of computational results). For example, the GNO recipe can be used by software to perform a set of calculations, the result of which will be an output specified by a recipe. In one embodiment, a result could be a thickness of a layer used in a semiconductor process (e.g. CMP, etching, etc.).

As described above, GNO technique 300 can advantageously use a finite number of samples and limited computational resources to build an accurate, empirical model. In one embodiment, GNO technique 300 can reduce computation time by as much as 50% compared to standard techniques.

Although illustrative embodiments of the invention have been described in detail herein with reference to the accompanying figures, it is to be understood that the invention is not limited to those precise embodiments. They are not intended to be exhaustive or to limit the invention to the precise forms disclosed. As such, many modifications and variations will be apparent. For example, a GNO technique can be used anytime when the best average representation is desired. For example, irrespective of grating structures being present, multiple spectra can be simultaneously fit to determine the average representation of the layer. If no grating structures are present, then the GNO technique is essentially solving for the refractive index, the thickness, and other properties of multiple films on a substrate. Thus, in general, if a layer is non-ideal (e.g. a graded refractive index or some other complex property) but can be represented by multiple variables, then solving for multiple variables with limited data can be performed, although subject to the correlation between those variables. Advantageously, in accordance with the principles of a GNO technique, multiple data sets (e.g. multiple spectra) can be simultaneously used to solve for those variables, thereby minimizing the correlation between those variables and ensuring accurate average values for those variables. Accordingly, it is intended that the scope of the invention be defined by the following Claims and their equivalents.

The invention claimed is:

1. A global node optimization (GNO) technique for generating a model for a planar multiple layer film stack structure, the GNO technique comprising:
   designating a design of experiment (DOE);
   obtaining spectra from the DOE;
   obtaining target thicknesses from the DOE;
   identifying a continuous film approximation (CFA) and a grating factor (GF) set using a GF lookup model, wherein the GF lookup model takes into account diffraction variables that vary with thickness, grating dimension or scattering, wherein the CFA is a mixing model, and wherein each grating factor introduces a correction at an interface of a binary layer of the DOE using a processor; and
   optimizing the model using the CFA and the GF set by simultaneously fitting a plurality of the spectra while minimizing error compared to the target thicknesses.

2. The GNO technique of claim 1, further including:
   determining whether the optimizing is acceptable; and
   if not, then returning to one of obtaining spectra, obtaining target thicknesses, and identifying the CFA and the GF set.

3. The GNO technique of claim 1, wherein the DOE includes a plurality of wafers.

4. The GNO technique of claim 1, wherein the spectra are obtained from at least 10 die on a wafer.

5. The GNO technique of claim 1, wherein the spectra include ellipsometric spectra in a wavelength range of 240-800 nm.

6. The GNO technique of claim 1, wherein the spectra and target thicknesses include in-die measurements.

7. The GNO technique of claim 1, wherein optimizing includes simultaneously fitting all of the plurality of the spectra.

8. The GNO technique of claim 1, further including creating a GNO stack after simultaneously fitting all of the plurality of the spectra, the GNO stack including mathematical models that describe physical properties of the film stack structure.

9. The GNO technique of claim 8, further including creating a GNO recipe using the GNO stack, the GNO recipe including ordered instructions using the mathematical models of the GNO stack to achieve at least one computational result.

10. A tool for implementing a global node optimization (GNO) technique, the GNO technique for generating a model for a planar multiple layer film stack structure, the tool comprising:

means for designating a design of experiment (DOE);

means for obtaining spectra from the DOE;

means for obtaining target thicknesses from the DOE;

means for identifying a continuous film approximation (CFA) and a grating factor (GF) set using a GF lookup model, wherein the GF lookup model takes into account diffraction variables that vary with thickness, grating dimension or scattering, wherein the CFA is a mixing model, and wherein each grating factor introduces a correction at an interface of a binary layer of the DOE using a processor; and means for optimizing the model using the CFA and the GF set by simultaneously fitting a plurality of the spectra while minimizing error compared to the target thicknesses.

* * * * *